United States Patent [19]

Lee et al.

[11] Patent Number: 5,571,528
[45] Date of Patent: Nov. 5, 1996

[54] PILOCARPINE-CONTAINING CHEWING GUM THAT STIMULATES SALIVATION

[76] Inventors: Sung-Woo Lee, 14-1201 Jindalle Apt., Yoksam 2-dong, Kangnam-ku, Seoul; Hong-Ryeol Ryu, 1410-4, Edo 1-dong, Cheju-shi, Cheju-do, both of Rep. of Korea

[21] Appl. No.: 496,216

[22] Filed: Jun. 28, 1995

[30] Foreign Application Priority Data

Jun. 30, 1994 [KR] Rep. of Korea ............ 94-15477

[51] Int. Cl.⁶ .................. A61K 9/68; A61K 9/28; A61K 47/30
[52] U.S. Cl. ............... 424/440; 424/439; 424/441; 514/772.3
[58] Field of Search ............... 424/439, 440, 424/441; 514/772.3

[56] References Cited

U.S. PATENT DOCUMENTS

| | | |
|---|---|---|
| 4,634,593 | 1/1987 | Stroz et al. . |
| 4,839,184 | 6/1989 | Cherukuri et al. . |
| 4,865,853 | 9/1989 | Mookherjee et al. . |
| 4,889,727 | 12/1989 | Dave et al. . |
| 4,908,211 | 3/1990 | Paz . |
| 4,983,405 | 1/1991 | Cherukuri et al. . |
| 5,156,866 | 10/1992 | Sato et al. . |

FOREIGN PATENT DOCUMENTS

| | | |
|---|---|---|
| 267160 | 5/1988 | European Pat. Off. . |
| 498463 | 8/1992 | European Pat. Off. . |
| 528466 | 2/1993 | European Pat. Off. . |
| 1320955 | 12/1989 | Japan . |
| 1300853 | 12/1989 | Japan . |
| 2242640 | 9/1990 | Japan . |
| 4158746 | 6/1992 | Japan . |
| 5276873 | 10/1993 | Japan . |
| 0662750 | 3/1994 | Japan . |
| 942648 | 3/1994 | Rep. of Korea . |
| 943470 | 3/1994 | Rep. of Korea . |
| 942868 | 4/1994 | Rep. of Korea . |
| 944561 | 5/1994 | Rep. of Korea . |

*Primary Examiner*—Carlos Azpuru
*Attorney, Agent, or Firm*—James Creighton Wray

[57] ABSTRACT

The present invention is a pilocarpine containing chewing gum for stimulating salivation. The invention contains 0.13–0.20 weight % of pilocarpine as well as normal gum base that includes sweetening agents and flavors. It can improve oral hygiene by stimulating parasympathetic innervation in salivary glands with pilocarpine solubilized in the oral cavity.

2 Claims, No Drawings

PILOCARPINE-CONTAINING CHEWING GUM THAT STIMULATES SALIVATION

BACKGROUND OF THE INVENTION

This invention is a pilocarpine-containing chewing gum that contains 0.13~0.20 weight % of pilocarpine as well as normal gum base that contains sweetening materials and flavors.

The purpose of the invention is for development of a new type of chewing gum that stimulates the salivation by solubilized pilocarpine from chewing gum, that acts on the parasympathetic nerve in the salivary glands.

Generally, chewing gum is just for enjoying chewing. The chewing gums for specific purposes have specific components for their specific functions. Various kinds of chewing gums for elimination of bad oral odor, for alarming sleeping, for producing specific flavors, and others are available.

Contrary to traditional chewing gums, the invented gum not only can provide fresh sensation and good taste by sweetening agents and flavors but also can improve oral hygiene and speaking ability by stimulating salivation.

The ability of salivation of the aged people in their sixties is one-eighth of that of young adults. In this dry mouth state, the number of microorganisms increases.

For example, there are 70,000/cm$^2$ of microorganisms in the oral cavity of young adults compared with 300,000/cm$^2$ in the mouth of aged people. This fact means bad oral hygiene and increased susceptibility to infectious diseases in aged population.

Therefore, aged people suffer from speaking difficulty and can not make exact pronunciation in dry mouth state. Digestive function is also decreased.

Dry mouth is often found in the people under stressful condition and with some diseases.

The decreased salivation with aging is a normal physiologic phenomenon. However, severe dry mouth can be found in congenital ectodermal developmetal disorders and Sjögren syndrome which usually occurs after the age of forties. There are over 100,000,000/ml microorganisms in saliva, and about one-third of them are pathogenic ones. Bacteriocidal and bacteriostatic effects of saliva are essential for sound oral health. Infection in various organs of body can occur in the decreased state and absence of salivation. Normal salivation provides maintenance of systemic body health as well as digestion and lubrication.

Parasympathetic stimulators have been used as traditional sialagogues and oral administration of pilocarpine(20 mg, twice a day) was popular regimen. (Drug information Handbook p.p. 926, LAXY COMP Inc. 1993. U.S.A.)

However, long term use of pilocarpine showed limitation in patients with hypertension, parkinsonism, and some related conditions because of stimulating effect of pilocarpine on the central nervous system(CNS) and myocardium. (reference:[1] Fox, P. C., Van Der Ven, P. F., Baum, Boj. and Mandel, I. D.: Pilocarpine for the treatment of xerostomia associated with salivary gland dysfuction, Oral Surg. 61(3): 243-248, 1986. [2] Deborah Greenspan & Troy E. Daniels: The use of pilocarpine in post-radiation xerostomia, LADR Abstracts 1979. [3] Martin M. Ferguson, Bsc, MBCHB, BDS, FDSRCPS.: Pilocarpine and other cholinergic drugs in the management of salivary gland dysfunction, oral medicine oral pathology, Vol. 75. No.2:186–190, 1993.)

SUMMARY OF THE INVENTION

The invented item can increase salivation by pilocarpine and chewing activity of gum. Thus, it is possible to improve oral hygiene and the functional ability of digestion and speaking.

DETAILED DESCRIPTION OF PREFERRED EMBODIMENTS

One pilocarpine-containing chewing gum contains 4~5 mg of pilocarpine and 2.5~3 g or base which is a mixture of styrene-butadiene copolymer, or chicle, rubber latex(major component of normal gum base), hydrogenated esterified rubber base, paraffin wax, stearic acid and xylitol(glycoalcohol). This means that oral chewing gum contains only one-fifth of the dosage of pilocarpine that is routinely used in oral administration. About 50% of pilocarpine solubilized in saliva penetrates oral mucosa, and acts on salivary glands during 20 minutes of chewing gum, indicating that only one-eight of 20 mg is active and that the chance of possible side effects can be minimized.

The pilocarpine absorbed systemically by chewing gum improves the functional capacity of sweat and lacrimal glands, that can be also helpful in dry skin and dryeye conditions. The pilocarpine that reaches into salivary glands directly through oral mucosa during gum chewing, stimulates salivation, which is helpful for the mechanical protection of oral mucosa, efficient mastication and speaking, and as a defense to pathogenic microorganisms by diluting microorganisms, self-cleansing effects, bacteriostasis, and bacteriocidal effects.

Therefore, pilocarpine-containing chewing gum (1) can improve physiologic functions of oral cavity such as speaking, digestion, and others and (2) can protect body from the infection of pathogenic oral microorganisms.

Pilocarpine ($C_{11}H_{16}O_2N_2$) used in this invention is an alkaloid found in the leaves of the plant Pilocarpus and can, be derived from histidine, one of natural amino acids. Pilocarpine is used to detoxify atropine intoxication and to increase sweating.

The invented item can not only provide fresh sensation by sweetening agents and flavors but, also increase salivation by stimulating the parasympathetic innervation in salivary glands with the aid of solubilized pilocarpine in oral cavity.

The increase of salivation can inhibit the growth of microorganisms and improve oral hygiene and the functional capability of speaking and digestion.

| Formula 1 | |
|---|---|
| Gum base: styrene-butadione copolymer | 30 Weight % |
| Pilocarpine: | 0.13~0.20 Weight % |
| Base: hydrogenated esterified rubber | 3 Weight % |
| Anti-gluing agent: paraffin wax | 5 Weight % |
| Softener: stearic acid | 2 Weight % |
| Sweetening agent: xylitol(glycoalcohol) | 59~60 Weight % |
| Formula 2 | |
| Gum base: chicle, latex rubber | 30 Weight % |
| Base: hydrogentated esterified rubber | 3 Weight % |
| Anti-gluing agent: paraffin wax | 5 Weight % |
| Softener: stearic acid | 2 Weight % |
| Sweetening agent: xylitol(glycoalcohol) | 60 Weight % |
| Pilocarpine: | 4~5 mg |

The materials mixed according to formula 1 of formula 2 were boiled and mixed homogenously, then cooled in room temperature. Sialogogue, 0.13~0.20 weight % of pilocarpine is then added homogenously and frozen to −5° C. Finally, the pilocarpine-containing chewing gum can be made by cutting the plate form of above material and packing.

We claim:

1. A pilocarpine-containing chewing gum comprising: 4~5 mg of pilocarpine and 2.5~3 g of a base material, and, said base material comprising:
a mixture of chicle, latex rubber (major component of a normal gum base), a hydrogenated esterified rubber base, paraffin wax, stearic acid, and xylitol(glycoalcohol).

2. A pilocarpine-containing chewing gum comprising: 0.13~0.20 weight % of pilocarpine and a gum base, and, said gum base comprising:
a mixture of 30 weight % of a styrene-butadiene copolymer, 3 weight % of a hydrogenated esterified rubber base, 5 weight % of paraffin wax, 2 weight % of stearic acid and 59~60 weight % of glycoalcohol.

* * * * *